US00PP17973P3

(12) United States Plant Patent

Jepsen et al.

(10) Patent No.: US PP17,973 P3

(45) Date of Patent: *Sep. 4, 2007

(54) *KALANCHOE* PLANT NAMED 'AFRICAN PEARL'

(50) Latin Name: ***K. blossfeldiana*×*K. laciniata* *interspecific* hybrid**
Varietal Denomination: AFRICAN PEARL

(75) Inventors: Knud Jepsen, Hinnerup (DK); Ellen Christensen, Hinnerup (DK)

(73) Assignee: Knud Jepsen A/S, Hinnerup (DK)

( * ) Notice: Subject to any disclaimer, the term of this patent is extended or adjusted under 35 U.S.C. 154(b) by 125 days.

This patent is subject to a terminal disclaimer.

(21) Appl. No.: 11/011,611

(22) Filed: Dec. 15, 2004

(65) Prior Publication Data

US 2006/0041982 P1 Feb. 23, 2006

(51) Int. Cl.
*A01H 5/00* (2006.01)

(52) U.S. Cl. ..... Plt./324

(58) Field of Classification Search ..... Plt./324, Plt./335

See application file for complete search history.

(56) References Cited

U.S. PATENT DOCUMENTS

| | | | | | |
|---|---|---|---|---|---|
| PP12,299 | P2 | | 12/2001 | Jepsen | |
| PP13,365 | P2 | | 12/2002 | Vlielander | |
| PP14,714 | P2 | * | 4/2004 | Vlielander | Plt./336 |
| PP15,509 | P2 | * | 2/2005 | Jepsen | Plt./341 |
| 2006/0041981 | P1 | * | 2/2006 | Jepsen et al. | Plt./335 |
| 2006/0041982 | P1 | * | 2/2006 | Jepsen et al. | Plt./335 |
| 2006/0130191 | A1 | * | 6/2006 | Jepsen et al. | 800/323 |

OTHER PUBLICATIONS

UPOV ROM GTITM Computer Database, GTI Jouve Retrieval Software 2006/05 Citation for 'KJ 2003 0638'.*

* cited by examiner

*Primary Examiner*—Kent Bell
(74) *Attorney, Agent, or Firm*—Foley & Lardner LLP

(57) ABSTRACT

A new and distinct *K. blossfeldiana*×*K. laciniata* interspecific hybrid plant named 'AFRICAN PEARL' characterized by a large number of petals per flower resulting in the double-type or multi-petalled trait; large petal size resulting in a large flowers; the hastate and dissected young and mature leaves; the different yellow-orange colors of petals; and the large number of flowers on each plant.

3 Drawing Sheets

Latin name of the genus and species of the claimed plant: *K. blossfeldiana*×*K. laciniata* interspecific hybrid.
Variety denomination: 'AFRICAN PEARL'.

BACKGROUND OF THE INVENTION

The present invention relates to a new and distinct cultivar of *Kalanchoe* plant, botanically known as *K. blossfeldiana*× *K. laciniata* interspecific hybrid, hereinafter referred to by the cultivar name 'AFRICAN PEARL'. As used herein, "interspecific hybrid" includes the progeny from the cross of two different species of *Kalanchoe,* as well as, the progeny resulting from subsequent backcrossing to one of the parents.

The genus of *Kalanchoe* belongs to the sedum family (Crassulaceae). There are more than 100 different species of *Kalanchoe,* of which more than 60 are found growing wild on Madagascar, many in South Africa and a few in Asia and South America. *Kalanchoe* belongs to the succulent plants, which are characterized by having turgid leaves. The leaves enable them to stand drought in nature or on the windowsill for a longer time than most other plants, and this allows for a supreme longevity.

The new *Kalanchoe* cultivar is a product of a controlled breeding program conducted by the Inventors, Knud Jepsen and Ellen Christensen, in Hinnerup, Denmark. The objective of the breeding program was to create new *Kalanchoe* cultivars with large flowers, numerous petals per flower, attractive flower coloration and excellent postproduction longevity.

The new *Kalanchoe* cultivar originated from a cross made in a controlled breeding program by the Inventors in Hinnerup, Denmark. The female parent is a proprietary selection of *K. blossfeldiana*×*K. laciniata* interspecific hybrid designated '2000 0716' having single-type flowers with 4 petals per flower. The female parent is described in U.S. Plant Pat. No. 15,509 and in European Union Community Variety Rights application serial No. 2003/0974, and is the second generation progeny of a fertile interspecific hybrid between *K. blossfeldiana* and *K. laciniata.* The male parent, designated *K. blossfeldiana* cultivar 'Monroe', is described in U.S. Plant Pat. No. 14,714, and has the multi-petalled double-type flower characteristic. The new *Kalanchoe* cultivar 'AFRICAN PEARL' was discovered and selected by the Inventors as a flowering plant within the progeny of the stated cross in a controlled environment in Hinnerup, Denmark.

Asexual reproduction of the new cultivar by vegetative terminal cuttings was first performed in February, 2004, in Hinnerup, Denmark, and has demonstrated that the combination of characteristics as herein disclosed for the new cultivar are firmly fixed and retained through successive generations of asexual reproduction. The new cultivar reproduces true-to-type through asexual reproduction.

BRIEF SUMMARY OF THE INVENTION

The following traits have been repeatedly observed and are determined to be basic characteristics of the new *Kalanchoe* cultivar 'AFRICAN PEARL' which in combination distinguish this *Kalanchoe* as a new and distinct cultivar:

1. large number of petals per flower resulting in a double-type or multi-petalled trait;
2. large size of petals resulting in a large flower;
3. the hastate, dissected leaves on young as well as mature leaves;
4. the different yellow-orange colors of petals; and
5. large number of flowers per plant.

The new *Kalanchoe* cultivar 'AFRICAN PEARL' has not been observed under all possible environmental conditions. The phenotype of the new cultivar may vary significantly with variations in environment such as temperature, light intensity, and day length without any change in the genotype of the plant. The following observations, measurements and values describe the new *Kalanchoe* cultivar 'AFRICAN PEARL' as grown in Hinnerup, Denmark, under conditions which closely approximate those generally used in commercial practice.

Plants of 'AFRICAN PEARL' differ from plants of the parental cultivars in the following characteristics:

| Trait | New Cultivar 'AFRICAN PEARL' | Female Parent '2000 0716' |
|---|---|---|
| Height of cultivar | About 31 cm | About 38 cm |
| Flower Type | Double-type | Single-type |
| Flower Diameter | 20-25 mm | 20-25 mm |
| Flower Number Per Plant | 250-300 | 500 |
| Number of Corolla Lobes | Up to 17 full or partial petals | 4 |
| Corolla Coloration | From outer to center of flower: First circle Yellow-orange, RHS 20D Next circle Yellow-orange, RHS 19B Center circle Yellow-orange, RHS 20D with a twist of red, RHS 39C Whole flower faints to light orange RHS 27C | Red-orange, RHS 44B |
| Shape of petal | The width of the petal is 9 mm. The length is 6 mm. The shape is ovate with mucronate apex. | The width of the petal is 10 mm. The length is 13 mm. The shape is obovate with cuspidate tip. |
| Leaf | Hastate, dissected leaves with a long petiole and long lamina. The leaf apex is obtuse and the base is cunate. | Hastate, dissected leaves with a long petiole and long lamina. The leaf apex is obtuse and the base is cunate. |
| Leaf texture | The foliage is glabrous and shining both above and below. | The foliage is glabrous and more shining above than below. |

-continued

| Trait | Male Parent 'Monroe' |
|---|---|
| Height of cultivar | About 24 cm |
| Flower Type | Double-type |
| Flower Diameter | 16-19 mm |
| Flower Number Per Plant | 350-400 |
| Number of Corolla Lobes | Up to 27 full or partial petals |
| Corolla Coloration | White, RHS 155 D |
| Shape of petal | The width of the petal is 4 mm. The length is 8 mm. The shape is ovate with cuspidate tip. |
| Leaf | Obovate leaves with obtuse leaf tips and truncate bases. The leaf margin is undulate. |
| Leaf texture | The foliage is glabrous and shining both above and below. |

Of the many commercial cultivars known to the present Inventors, the most similar in comparison to 'AFRICAN PEARL' is parental cultivar 'KJ 2000 0716'. Comparing these two cultivars, the main distinction is the form and the color of the flower, as described in the preceding table.

BRIEF DESCRIPTION OF THE DRAWINGS

The accompanying photographs illustrate the overall appearance of the new *Kalanchoe* cultivar 'AFRICAN PEARL' showing the colors as true as is reasonably possible with colored reproductions of this type.

FIG. 1 shows a top perspective view of a typical potted flowering plant of 'AFRICAN PEARL', 18 weeks after planting of cutting.

FIG. 2 shows a side perspective view of a typical potted flowering plant of 'AFRICAN PEARL', 18 weeks after planting of cutting.

FIG. 3 shows the following typical plant parts of 'AFRICAN PEARL': A Inflorescence; B. Flower, just opened; C. Flower opened one week, D. Flower bud, top; E. Inside a flower; F. Flower bud, site; G. Petal; H. Pistil; I. Sepal; J. Mature leaf; and K. Young leaf.

DETAILED BOTANICAL DESCRIPTION

'AFRICAN PEARL' has not been observed under all possible environmental conditions. The phenotype of the new cultivar may vary significantly with variations in environment such as temperature, light intensity, and day length without any change in the genotype of the plant.

The aforementioned photographs, together with the following observations, measurements and values describe the new *Kalanchoe* cultivar as grown in a greenhouse in Hinnerup, Denmark, under conditions which closely approximate those generally used in commercial practice. The plants were grown in a greenhouse at 64.4° F. at daytime and 68° F. during the night. The cultivar was produced in a either a 10.5 or 13 cm pot. The cuttings were grown in a long day (16 hours light, 8 hours dark) for the first 5 weeks. At week 6 after planting, the cultivar is grown in a short day (10 hours light, 14 hours dark). After 14 weeks the cultivar would be ready for sale. The cultivar was grown under natural light conditions supplemented with 70 $\mu mol/m^2/s$ SON-T light when the natural light was less than 100 $\mu mol/m^2/s$. At short day, the flowering was induced. The reaction time from day of induction to day of first opened flower was 67 days. The peat based soil mix was watered with a solution containing 200 parts per million (ppm) nitrogen, 200 ppm potassium and 40 ppm phosphorous, 200 ppm calcium, 40 ppm magnesium, 60 ppm sulphate, 1 ppm iron, 0.6 ppm manganese, 0.1 ppm copper, 0.1 ppm zink, 0.3 ppm borium, 0.03 ppm molybdenum.

In following description, color references are made to The Royal Horticultural Society Colour Chart (R.H.S.), published 1986, except where general colors of ordinary significance are used. Color values were taken under daylight conditions at approximately 12 a.m. in a greenhouse in Hinnerup, Denmark. The age of the plant described is 15 weeks (from the time the cutting was planted in growth medium to when the picture was taken).

Parentage:

*Male or pollen parent.*—*K. blossfeldiana* cultivar 'Monroe' (disclosed in U.S. Plant Pat. No. 14,714).

*Female or seed parent.*—*K. blossfeldiana*×*K. laciniata* interspecific hybrid cultivar '2000 0716' (disclosed in U.S. Plant Pat. No. 15,509).

Classification:

*Botanical.*—*Kalanchoe* interspecific hybrid×*K. blossfeldiana* cultivar 'AFRICAN PEARL' ($2^{nd}$ generation after *K. blossfeldiana*×*K. laciniata* interspecific hybrid back-crossed with *K. blossfeldiana*).

Propagation: Vegetative terminal cuttings.

*Rooting habit.*—The cultivar has numerous, branched, fine and fibrous roots.

*Time to initiate roots.*—It takes between one and two weeks to initiate roots.

*Time to produce a rooted cutting.*—It will take three weeks to produce a well rooted cutting. In winter time, it can take one week more.

Plant: If the plants are grown according to the description above, it will perform as described below. Variation from this should be expected over the course of the year, and if the physical growing conditions varies from the description.

*Growth habit.*—This cultivar is upright and uniform. The flowers are formed above the top of the leaf canopy, but flowers will also appear between the leaves. The flowers are assembled in numerous compound inflorescences.

*Growth rate.*—Ready for sale after 16 weeks.

*Branching habit and description.*—Freely branching; typically 4 to 8 lateral branches develop per plant. Pinching (removal of the terminal apex) is not mandatory, but will enhance lateral branching. When grown in 10 cm pots the cultivar is not pinched.

*Height at flowering.*—The height of the cultivar is about 31 cm, from the bottom of the pot to the top of the plant, depending on growth conditions.

*Spread/diameter at flowering.*—The diameter at flowering is about 30 cm.

Stems:

*Appearance.*—The cultivar has around 8 stems with none, one or numerous leaf pairs on the stem. The inflorescence on the top of the flower stem is branched, giving an inverted triangle with a rounded crown. Each branch has between 40 and 60 flowers.

*Aspect.*—The stem is strong.

*Length.*—The length of the stem is about 14 cm depending on growth conditions.

*Texture.*—The texture of the stem is glabrous and shining.

*Color.*—The color of the stem is yellow-green, RHS 146 A.

Foliage:

*Arrangement.*—The foliage is yellow-green with the same colors of the immature as well as the mature leaf, RHS 146 A and RHS 147 A. The majority of the leaves are at the base of the plant, but immature leaves appear also on the flowering stem.

*Overall shape of leaf.*—The leaves are defined as hastate, dissected leaves.

*Apex.*—The form of the apex is obtuse.

*Base.*—The form of the base is cunate.

*Length.*—The length of the foliage varies from about 3 cm for an immature leaf to about 14 cm for a mature leaf.

*Width.*—The width varies from about 2 cm for an immature leaf to about 13 cm for a mature leaf.

*Margin.*—The foliage has a dentate margin.

*Texture.*—The foliage is glabrous and shining both above and below.

*Color of upper surface.*—Mature leaf: The color of the mature leaf is dark yellow-green and is closely described with RHS 147 A. Immature leaf: The immature leaf has the same color as the mature leaf, dark yellow-green, described with RHS 147 A.

*Color of lower surface.*—Mature leaf: The color of the lower surface is different from the upper surface, and is closely described with a dark yellow-green color between RHS 146 A and RHS 147 A. Immature leaf: The immature leaf has the same color as the mature leaf, dark yellow-green, and is closely described with a dark yellow-green color between RHS 146 A and RHS 147 A.

*Venation color.*—There is no visual appearance of veins. Upper surface: There is no difference between the color of venation and the rest of the leaf. Lower surface: There is no difference between the color of venation and the rest of the leaf.

*Petiole.*—Length: The length of the petiole varies between an immature and mature leaf. The length of an immature leaf varies between 0.5 and 1 cm. The length of a mature leaf varies between 3 and 3.5 cm. Diameter: The diameter of petiole varies between an immature and mature leaf. The diameter of an immature leaf is 4 mm. The diameter of a mature leaf is 5 mm. Color: There is no difference between the color of petiole and the rest of the leaf.

Flower description:

*Flower type and habit.*—The flower type is a double-type with 16 to 19 petals per flower. The average number of petals per flower is 17.

*Natural flowering season.*—The flowering season is year round, when grown according to description above. When planting outside the flowering season will be in the summer (April to October), depending on local climatic conditions.

*Time to flower.*—The time from start of short day treatment to $1^{st}$ flower is about 74 days, approximately 1 week longer in winter time.

*Flowering stem length.*—The length of the flowering stem is ranging from 13 to 14 cm depending on the growth conditions.

*Post production longevity.*—'AFRICAN PEARL' maintain good leaf and flower substance for at least 6 weeks under interior environmental conditions.

*Winter hardiness/weather tolerance.*—'AFRICAN PEARL' withstands wind, rain and direct sunlight, and can cope with temperatures between 40 and 95 degrees F.

*Fragrance.*—'AFRICAN PEARL' has no fragrance.

*Flower size.*—The diameter of the flower range from is 2.5 to 3 cm.

*Overall shape.*—The shape is rose-like, defined by at least 5 petals per flower.

*Quantity.*—'AFRICAN PEARL' produces a large number of flower ranging from 200 to 250 flowers per plant.

*Bud.*—Rate of opening: From the time when the bud is showing color, the flower will open within 10 days. Color: At the tip the bud is yellow-green, RHS 145 B, with a twist of orange 24 A. At the base the bud has the same yellow-green color, RHS 145 B. Shape: The shape of the bud is ellipsoidal with the smallest diameter towards the base. Length: The length of the bud is about 1.5 cm. Diameter: The diameter of the bud is about 8 mm at the tip and about 4 mm at the base.

*Petal.*—Quantity: Typically 16–17 fused at the base. Shape: The shape of petal is oval. Length: The length is about 9 mm. Width: The width is about 6 mm. Apex: The shape of apex is mucronate. Margin: The shape of the margin can be described as entire. Texture: The texture of the petals is soft, smooth and matte. Color when opening: Upper surface: The color of the upper surface of the petals can be described as follows: Going from the outer circle to the inner circle of petals, the first circle of petals is yellow-orange, RHS 20 D, the next is yellow-orange, RHS 19 B, and the middle is yellow-orange, RHS 20 B, with a touch of red, RHS 39 C. Lower surface: The color of the lower surface of the petals is yellow-orange, RHS 23 D, with a touch of red, RHS 38 A. Color when fully open: Upper surface: At maturing the upper surface of the whole flower fades to orange RHS 27 C. Lower surface: At maturity the lower surface of the whole flower fades to orange RHS 27 C.

*Sepal.*—Quantity: Typically 4 sepals fused at the base. Shape: The shape of sepal is lanceolate. Length: The length is 10 mm. Width: The width is 3 mm. Apex: The shape of the apex is acute. Margin: The shape of the margin is entire. Texture: The texture of the sepals is glabrous and shining. Color when opening: Upper surface: The upper surface of the sepal is green, RHS 137 B. Lower surface: The lower surface of the sepal is green, RHS 137 B. Color when fully open: Upper surface: The upper surface of the sepal is green, RHS 137 B. Lower surface: The lower surface the sepal is green, RHS 137 B.

*Peduncle.*—Length: Every flower has a peduncle with a length of 5 mm. Color: The peduncle is yellow-green; RHS 146 A. Texture: The peduncle is glabrous and shining.

Reproductive organs:

*Stamen.*—Number: The flower has between 7 to 9 stamens. Color: The color of the stamens is greyed-orange, RHS 177 B.

*Anthers.*—Number: The number of anthers is 7 to 9. Size: The anthers are less than 1 mm in length. Color: The color of the anthers is yellow-brownish, RHS 14 B.

*Filament color.*—The color of the filament is yellow-green, RHS 145 C.

*Pollen color.*—The color of the pollen is yellow, RHS 17 C.

*Pollen amount.*—A medium amount of pollen with very good pollen fertility of 100% depending on time of year.

*Pistil.*—Number: The number of pistils is four.

*Stigma.*—Shape: The shape of the stigma is round. Color: The color of the stigma is yellow-green, RHS 145 A.

*Style.*—Shape: The shape of the style is thin and cylindrical. Color: The color of the style is yellow-green, RHS 145 A.

*Ovary.*—Color: The color of ovary is green, RHS 144 B.

*Seeds.*—Number: Between 50 and 60 potential seeds per ovary. Width: The width of the seeds is less than 0.5 mm. Length: The length of the seeds is less than 1 mm. Shape: The shape of the seeds is ellipsoidal. Color: The color of the potential seeds is green, RHS 145 C.

*Fruit* (*ovary*).—Shape: The shape of the fruit is cylindrical. Width: The width of the fruit is 1 mm. Length: The length of the fruit is 6 mm. Color: The color of the fruit is yellow green, RHS 145 A.

Disease resistance/susceptibility: No information on disease resistance or susceptibility is currently available.

We claim:

1. A new and distinct *K. blossfeldiana*×*K. laciniata* interspecific hybrid plant named 'AFRICAN PEARL', substantially as illustrated and described herein.

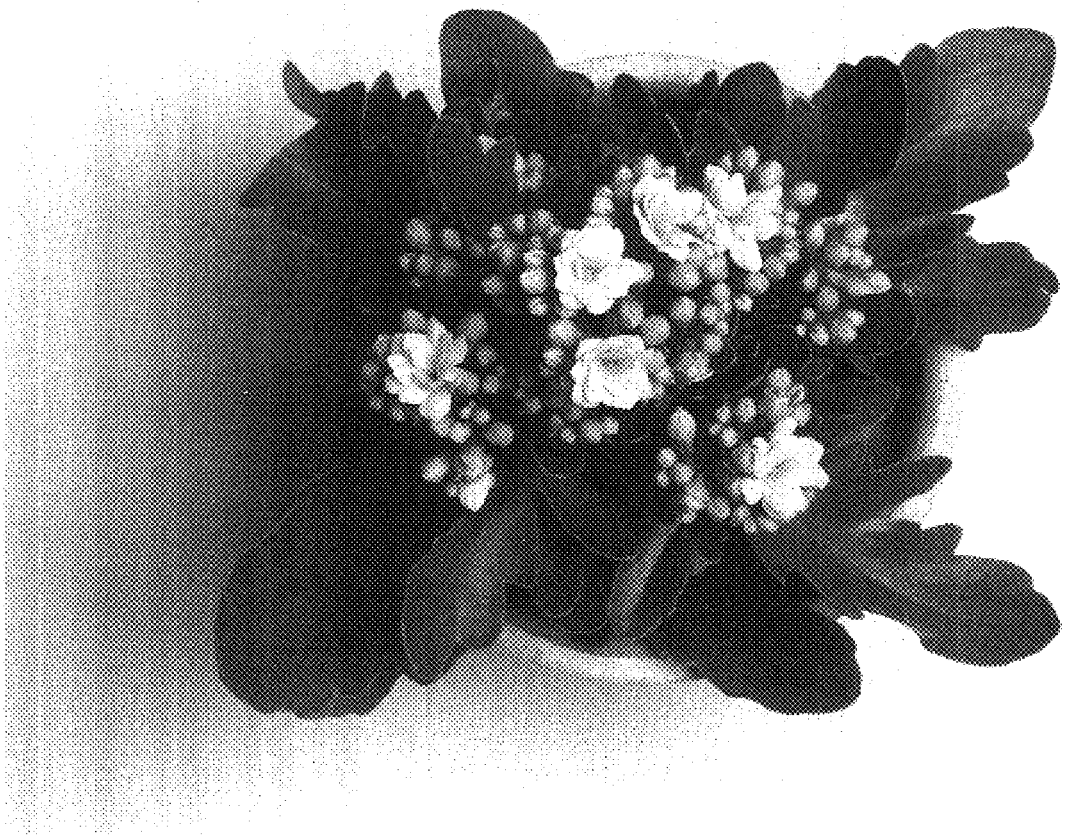

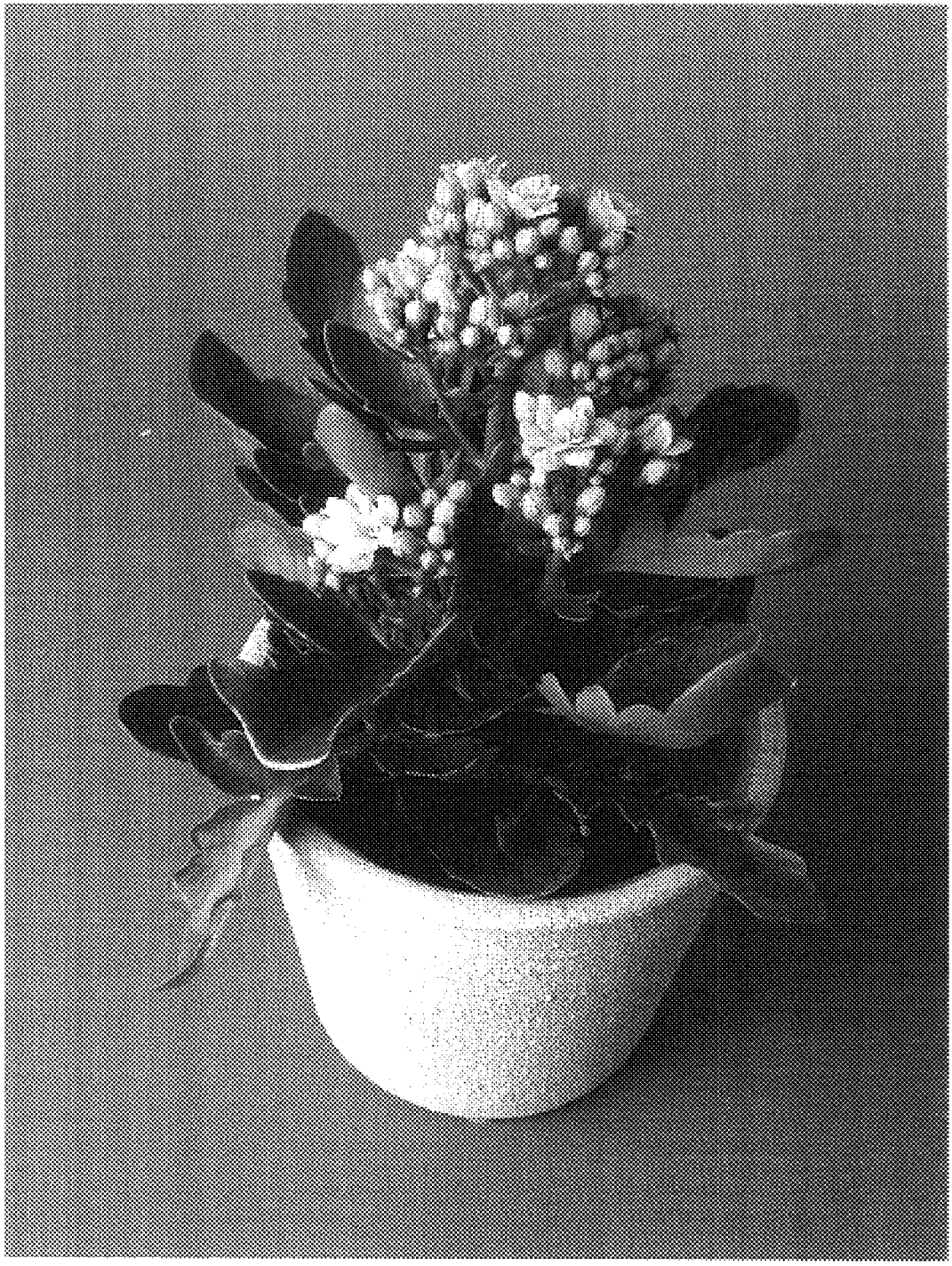

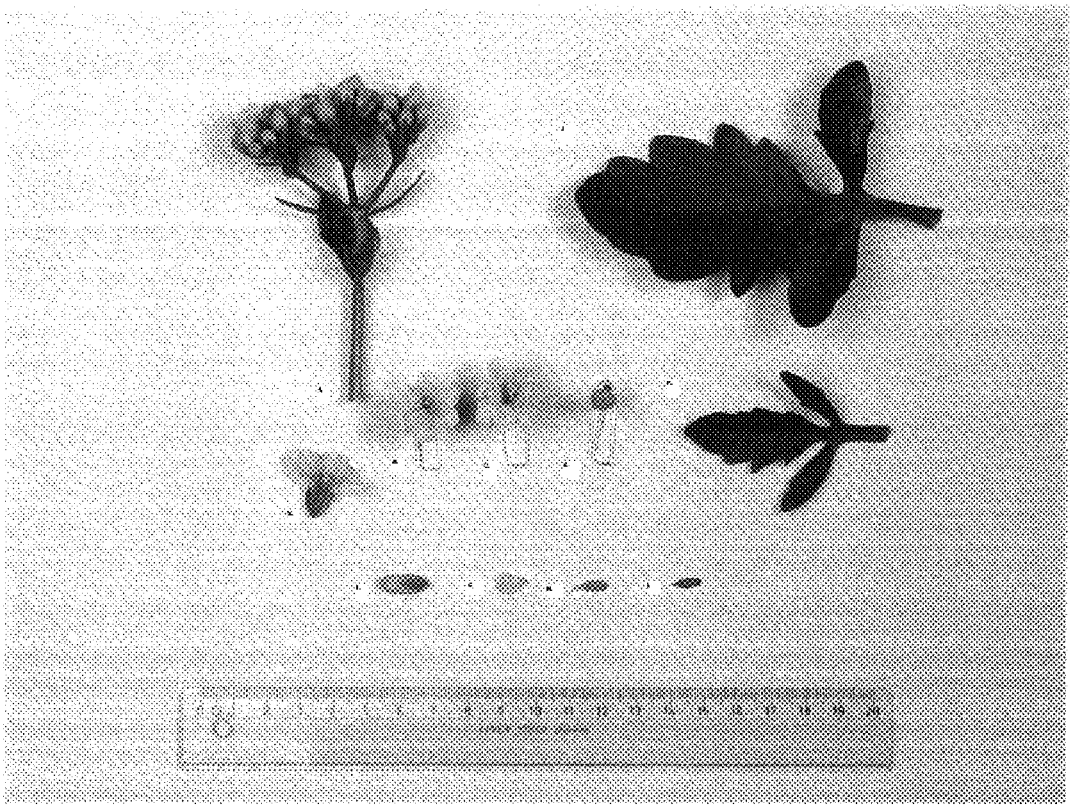

* * * * *